US00PP08610P

United States Patent [19]

VandenBerg

[11] Patent Number: Plant 8,610

[45] Date of Patent: Feb. 22, 1994

[54] CHRYSANTHEMUM PLANT NAMED YELLOW CHANTAL

[75] Inventor: Cornelis P. VandenBerg, Salinas, Calif.

[73] Assignee: Yoder Brothers Inc., Barberton, Ohio

[21] Appl. No.: 826,069

[22] Filed: Jan. 27, 1992

[51] Int. Cl.[5] ..... A01H 5/00

[52] U.S. Cl. ..... Plt./82.2

[58] Field of Search ..... Plt. 82.2

[56] References Cited

U.S. PATENT DOCUMENTS

| | | | |
|---|---|---|---|
| Plt. 7673 | 10/1991 | VandenBerg | Plt. 82.2 |
| Plt. 7600 | 7/1991 | VandenBerg | Plt. 82.2 |
| Plt. 6954 | 7/1989 | VandenBerg | Plt. 82.2 |
| Plt. 6943 | 7/1989 | VandenBerg | Plt. 82.2 |
| Plt. 6399 | 11/1988 | Duffett et al | Plt. 82.1 |
| Plt. 6881 | 6/1989 | VandenBerg | Plt. 82.1 |
| 4,616,099 | 10/1986 | Sparkes | 47/58 |

OTHER PUBLICATIONS

Broertjes, et al., 1980, "A mutant of a mutant . . . Irradiation of progressive radiation-induced mutants in a mutation breeding programme with *Chrysanthemum morifolium*", Euphytica, 29:526-530.

Gosling, ed., 1979, "The Chrysanthemum Manual-6th edition", The National Chrysanthemum Society, London, Essex Telegraph Press, Ltd., pp. 329-336.

Broertjes, et al., 1978, "Application of Mutation Breeding Methods In the Improvement of Vegetatively Propagated Crops", Elsevier Sci. Pub. Co., New York, pp. 162-175.

Searle, et al., 1968, "Chrysanthemums The Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of Chrysanthemums", Euphytica, 15:156-162.

Dowrick et al., 1966, "The induction of mutations in Chrysanthemum using X- and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Yellow Chantal particularly characterized by its flat capitulum form; daisy capitulum type; yellow ray floret color; diameter across face of capitulum of 25 to 28 mm when fully opened, when grown as a pinched spray pot mum; photoperiodic flowering response to short days of 46 to 49 days; plant height, with 14 to 15 long days after sticking unrooted cuttings, and with 0 to 1 applications of 2500 ppm B-9 SP, ranges from 18 to 20 cm when grown as a pinched pot mum with 4 cuttings in a 15 cm pot; small dark green foliage; branching pattern is spreading and very prolific, each plant having 6 to 8 laterals after pinch; very floriferous, with an excellent display of many small flowers; and excellent tolerance to high temperatures for bud initiation and flower development.

1 Drawing Sheet

1

The present invention relates to a new and distinct cultivar of Chrysanthemum, botanically known as *Dendranthema grandiflora*, and referred to by the cultivar name Yellow Chantal.

Yellow Chantal, identified as 4147 (86-671B01), is a product of a mutation induction program. The new cultivar was discovered and selected by Cornelis P. VandenBerg on Mar. 20, 1990 in a controlled environment in Salinas, Calif., as one flowering plant within a flowering block established as rooted cuttings from stock plants which had been exposed as unrooted cuttings to an X-ray source of 1750 rads in Fort Myers, Fla., on Aug. 24, 1989. The irradiated parent cultivar was the cultivar identified as Chantal, disclosed in U.S. Plant Pat. No. 7,516, and described as a daisy spray pot mum with a flat capitulum form; a white ray floret color; diameter across face of capitulum of 25 to 28 mm when fully opened; flowering response period of 45 to 50 days after start of short days; plant height of 18 to 25 cm with 0 to 1 applications of 2500 ppm B-9 SP when grown as a pinched pot mum in a 15 cm pot; small dark green foliage; spreading and very prolific branching pattern, with 6 to 8 laterals after pinch; very floriferous, with an excellent display of many small flowers; and excellent tolerance to high temperatures for bud initiation and flower development.

The irradiation program resulting in Yellow Chantal had as its primary objective the expansion of color ranges of the parent cultivar Chantal. The irradiation

2 program comprised irradiating cuttings of the parent cultivar at irradiation levels of 1500, 1750 and 2000 rads. A total of 1762 cuttings harvested from a total of 225 irradiated plants were planted on Jan. 1, 1990, Dec. 11, 1989 and Nov. 27, 1989. Of these, 11 initial selections were made, which selections were then revegetated and reflowered. Three consecutive flowerings resulted in discarding 9 of the original 11 selections on Dec. 7, 1990. Two selections were retained and will be introduced as Yellow Chantal and Cream Chantal, the latter being disclosed in pending application Ser. No. 07/826,066.

The first act of sexual reproduction of Yellow Chantal was accomplished when vegetative cuttings were taken from the initial selection in May 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Chantal are firmly fixed and are retained through successive generations of asexual reproduction.

Yellow Chantal has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Yellow Chantal, which, in combination, distinguish this Chrysanthemum as a new and distinct cultivar:

1. Flat capitulum form.
2. Daisy capitulum type.
3. Yellow ray floret color.
4. Diameter across face of capitulum of 25 to 28 mm when fully opened, when grown as a pinched spray pot mum.
5. Photoperiodic flowering response to short days of 46 to 49 days.
6. Plant height, with 14 to 15 long days after sticking unrooted cuttings, and with 0 to 1 applications of 2500 ppm B-9 SP, ranges from 18 to 20 cm when grown as a pinched pot mum with 4 cuttings in a 15 cm pot.
7. Small dark green foliage.
8. Branching pattern is spreading and very prolific, each plant having 6 to 8 laterals after pinch.
9. Very floriferous, with an excellent display of many small flowers.
10. Excellent tolerance to high temperatures for bud initiation and flower development.

The accompanying photographic drawing is a side view of a potted mum of Yellow Chantal, with 4 cuttings in a 15 cm pot, with the colors being as nearly true as possible with illustrations of this type.

Of the commercial cultivars known to the inventor, the most similar in comparison to Yellow Chantal is the parent Chantal. All traits of Yellow Chantal are similar to those of Chantal, except for the ray floret color. Chantal has a clear white ray floret color, white Yellow Chantal has a yellow ray floret color. When compared to Cream Chantal, disclosed in pending application Ser. No. 07/826,066, Yellow Chantal has been two days slower in flowering response than Cream Chantal, with the flower size of Yellow Chantal being 1.5 mm larger than the flower size of Cream Chantal.

In the following description color references are made to The Royal Horticultural Society Colour Chart. The color values were determined on plant material grown as a pinched spray pot mum in Salinas, Calif. on Jul. 22, 1991.

CLASSIFICATION

*Botanical.*—*Dendranthema grandiflora* cv Yellow Chantal.

*Commercial.*—Flat daisy spray pot mum.

INFLORESCENCE

A. Capitulum:

*Form.*—Flat.

*Type.*—Daisy.

*Diameter across face.*—25 to 28 mm when fully opened.

B. Corolla of ray florets:

*Color (general tonality from the distance of three meters).*—Yellow.

*Color (upper surface).*—5B.

*Color (under surface).*—5C.

*Shape.*—Straight, oblong, concave.

C. Corolla of disc florets:

*Color (mature).*—Closest to 12A.

*Color (immature).*—Closest to 7A.

D. Reproductive organs:

*Androecium.*—Present on disc florets only; moderate pollen.

*Gynoecium.*—Present on both ray and disc florets.

PLANT

A. General Appearance:

*Height.*—18 to 20 cm when grown as a pinched pot mum with 14 to 15 long days after sticking unrooted cuttings, and with 0 to 1 applications of 2500 ppm B-9 SP.

*Branching pattern.*—Spreading and very prolific, each plant having 6 to 8 laterals after pinch.

B. Foliage:

*Color (upper surface).*—147A.

*Color (under surface).*—147B.

I claim:

1. A new and distinct Chrysanthemum plant named Yellow Chantal, as described and illustrated.

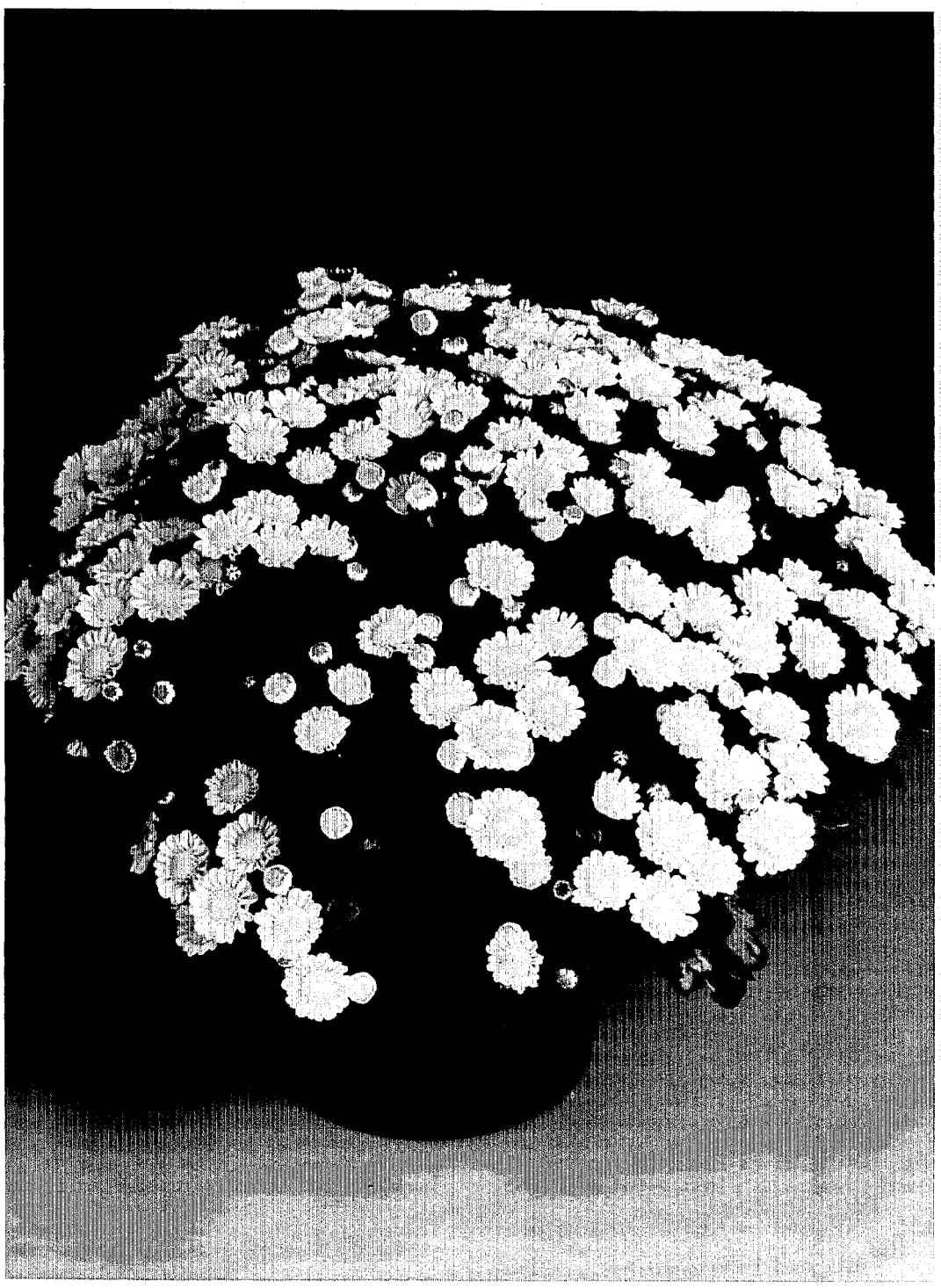

* * * * *